US005338845A

United States Patent [19]
Barrow et al.

[11] Patent Number: 5,338,845
[45] Date of Patent: Aug. 16, 1994

[54] ASPERGILLUS SPECIES, CYCLIC DIMERIC DIPEPTIDE DERIVATIVE SUBSTANCE P ANTAGONIST BIOSYNTHETIC PRODUCTS THEREOF, AND PROCESS FOR PREPARATION THEREOF

[75] Inventors: Colin J. Barrow, East Pikeland Township, Chester County, Pa.; James E. Brownell; David R. Houck, both of Colonie, N.Y.; Anderson C. Hong, Taipei, Taiwan; Janet L. Popp, Upper Providence Township, Montogmery County, Pa.; David M. Sedlock, Bethlehem, N.Y.

[73] Assignee: Sterling Winthrop Inc., New York, N.Y.

[21] Appl. No.: 984,668

[22] Filed: Dec. 2, 1992

[51] Int. Cl.⁵ .................. C07D 519/00; A61K 31/495

[52] U.S. Cl. .................... 544/343; 435/127
[58] Field of Search ...................... 544/343

[56] References Cited

PUBLICATIONS

Minato, J Chem. Soc Perkins I, p. 1819 (1973).
Springer et al., Tetrahedron Letters No. 28, pp. 2403–2406, 1977.

*Primary Examiner*—Mark L. Berch
*Attorney, Agent, or Firm*—Liza D. Hohenschutz

[57] ABSTRACT

A novel Aspergillus species, cyclic dimeric dipeptide derivatives which are biosynthetic products thereof and are useful as Substance P antagonists and therefore as analgesic and/or antiinflammatory agents, and a process for preparation of the biosynthetic products are disclosed.

4 Claims, No Drawings

ASPERGILLUS SPECIES, CYCLIC DIMERIC DIPEPTIDE DERIVATIVE SUBSTANCE P ANTAGONIST BIOSYNTHETIC PRODUCTS THEREOF, AND PROCESS FOR PREPARATION THEREOF

BACKGROUND OF THE INVENTION

1. Field of the Invention

The invention relates to a novel Aspergillus species, cyclic dimeric dipeptide derivatives which are biosynthetic products thereof and are useful as Substance P antagonists and therefore as analgesic and/or antiinflammatory agents, and to a process for preparation of the biosynthetic products.

2. Information Disclosure Statement

Springer et al. (Tetrahedron Letters No. 28, pp. 2403–2406, 1977) describes ditryptophenaline having the structural formula

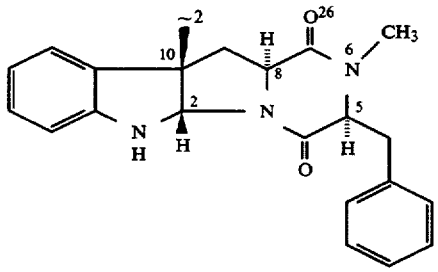

as a secondary metabolite of *Aspergillus flavus* "which possesses neither significant toxic ($LD_{50} > 200$ mg/kg) nor antibiotic properties".

Ditryptophenaline has the S-configuration at each of the four carbon atoms identified in the foregoing structural formula as "2" and "10" and as shown by the inventors below has only weak potency as an antagonist of Substance P. As also shown below the invention involves the remarkable discovery that a novel microorganism of the same genus produces by a novel process novel compounds having opposite configuration at the corresponding four carbon atoms and lacking methyl at each of the two nitrogen atoms identified in the foregoing structural formula as "6" and that the novel compounds are potent antagonists of Substance P.

SUMMARY OF THE INVENTION

In a first composition of matter aspect the invention is a pure culture of Aspergillus ATCC 74177.

In a second composition of matter aspect the invention is a compound having the structural formula

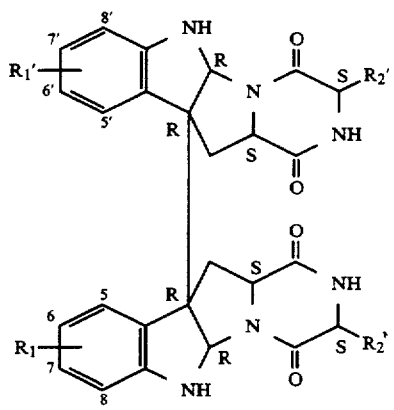

Formula I wherein $R_1$ and $R_1'$ are the same or different and are selected from the group consisting of hydrogen, halo, lower-alkyl and lower-alkoxy;

$R_2$ and $R_2'$ are the same or different and are selected from the group consisting of phenyl-lower-alkyl wherein phenyl is unsubstituted or substituted by halo or lower-alkyl, lower-alkyl except methyl, lower-alkylthio-lower-alkyl, trifluoromethyl-lower-alkyl, lower-alkenyl, thienyl-lower-alkyl and lower-cycloalkyl-lower-alkyl; and R and S represent in each instance the steric configuration of the adjacent carbon atom.

The compounds of Formula I are useful as Substance P antagonists and therefore as analgesic and/or antiinflammatory agents.

In a process aspect the invention is the process for producing a compound of Formula I which comprises (a) incubating Aspergillus ATCC 74177 mycelium on a lactose-corn steep liquor-peptone-agar medium at 25° to 30° C. for about 7 days, washing the resulting spores from the medium with a lactose-glycerol-water freezing solution, and optionally storing the resulting spore mixture at −20° C. or below;

(b) inoculating with the spore mixture a tenfold to thirtyfold volume of a glucose-cottonseed meal-yeast extract medium, incubating the resulting mixture at 25° to 30° C. for about 1 day with agitation, transferring the resulting mixture to a tenfold to twentyfold volume of a glycerol-beef extract medium, and incubating the resulting mixture at 25° to 30° C. for about 2 days with agitation to produce a cell culture; and (c) inoculating with the cell culture a fivefold to fifteenfold volume of a glycerol-beef extract medium, incubating the resulting mixture at 25° to 30° C. with agitation, extracting the resulting mixture, and isolating from the resulting extract the compound of Formula I wherein $R_1$ and $R_1'$ are both hydrogen and $R_2$ and $R_2'$ are both phenylmethyl; or (d) adding directly to the cell culture, or first inoculating with the cell culture a fivefold to fifteenfold volume of a glycerol-ammonia-glutamate medium or washing the cell culture twice with a twofold volume and resuspending it in a onefold volume of an aqueous 3-(4-morpholino)propanesulfonic acid buffer and then adding thereto, the compound having the structural formula

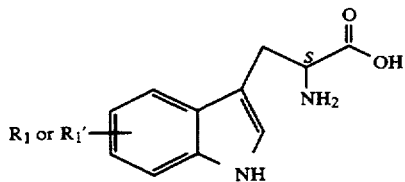

Formula II or a mixture thereof wherein $R_1$ and $R_1'$ are different, wherein $R_1$, $R_1'$ and S have the same meanings set forth above for Formula I, and the compound having the structural formula

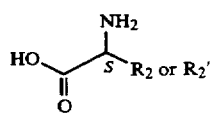

Formula III or a mixture thereof wherein $R_2$ and $R_2'$ are different, wherein $R_2$, $R_2'$ and S have the same meanings set forth above for Formula I, incubating the resulting mixture at 25° to 30° C. for 3 to 10 days with agitation, extracting the resulting mixture, and isolating from the resulting extract the corresponding compound of Formula I.

DETAILED DESCRIPTION OF THE INVENTION

Definitions

In $R_1$, $R_1'$, $R_2$ and $R_2'$ halo is fluoro, chloro, bromo or iodo. Lower-alkyl, lower-alkoxy or lower-alkenyl has from one or two to four carbon atoms and is branched or unbranched. Cycloalkyl has from three to seven carbon atoms. When $R_1$ or $R_1'$ is halo, it is for example 5 or 5'-fluoro, 6 or 6'-fluoro, 7 or 7'-fluoro or 6-bromo. When $R_1$ or $R_1'$ is lower-alkyl, it is for example 5 or 5'-methyl, 6 or 6'-methyl or 7-methyl. When $R_1$ or $R_1'$ is lower-alkoxy, it is for example 6-methoxy. When $R_2$ or $R_2'$ is phenyl-lower-alkyl, it is for example phenylmethyl (benzyl). When phenyl of phenyl-lower-alkyl is substituted by halo, it is for example 2-fluorophenyl, 3-fluorophenyl, 2-chlorophenyl or 4-chlorophenyl. When phenyl of phenyl-lower-alkyl is substituted by lower-alkyl, it is for example 2-methylphenyl or 4-methylphenyl. When $R_2$ or $R_2'$ is lower-alkyl, it is for example propyl, 1-methylethyl or 2-methylpropyl. When $R_2$ or $R_2'$ is lower-alkylthio-lower-alkyl, it is for example methylthiomethyl. When $R_2$ or $R_2'$ is trifluoromethyl-lower-alkyl, it is for example 2-trifluoromethylpropyl. When $R_2$ or $R_2'$ is lower-alkenyl, it is for example 2-propenyl or 2-butenyl. When $R_2$ or $R_2'$ is thienyl-lower-alkyl, it is for example 2-thienylmethyl. When $R_2$ or $R_2'$ is cycloalkyl-lower-alkyl, it is for example cyclohexylmethyl.

The Microorganism

Aspergillus ATCC 74177, a fungal species which was deposited on Jul. 30, 1992 with the American Type Culture Collection, 12301 Parklawn Drive, Rockville, Md. 20852, was isolated in Tainan Hsien, Taiwan in Lung Tien loam from a mengo rhizosphere. The soil sample was dried at room temperature for five days, heated at 100° C. for one hour, and plated on arginine-glycerol-vitamin agar containing cycloheximide (50 μg/mL), nystatin (50 μg/mL), penicillin G (1 μg/mL) and polymyxin B sulfate (5 μg/mL) at 27° C. for 17 days in preparation for culturing.

Taxonomically Aspergillus ATCC 74177 has been placed in the Aspergillus versicolor group, possibly Aspergillus sydowii or a close relative, based on the following description. Colonies are blue-green with a white margin, becoming a darker teal gray with age. Conidial heads are globose and radiate in loose columns. Simple metulae are generally present. Conidiophores are smooth, with ornamented, roughened conidia; no foot cells were observed. No telepmorph or sclerotia were present after three weeks.

Mutants of Aspergillus ATCC 74177 can be prepared, for example by use of x-ray radiation or ultraviolet radiation or nitrogen mustards, and can be cultured to produce the compounds of Formula I.

PRODUCTION OF THE COMPOUNDS

In the process aspect of the invention "corresponding" means that a variable in one structural formula has the same meaning in another structural formula.

Process step (a) is carried out using Aspergillus ATCC 74177 in the form of frozen lactose-corn steep liquor-peptone-agar plugs thereof containing mycelium. The lactose-corn steep liquor-peptone-agar medium for the slants has the following formula and is adjusted to pH 4.8 prior to autoclaving:

| Lactose-Corn Steep Liquor-Peptone-Agar Medium | |
|---|---|
| Ingredient | % Weight/Volume |
| lactose | 1.5 |
| corn steep liquor | 0.5 |
| peptone | 0.5 |
| NaCl | 0.4 |
| $MgSO_4.7H_2O$ | 0.05 |
| $KH_2PO_4$ | 0.06 |
| $FeCl_3.6H_2O$ | 0.0005 |
| $CuSO_4.5H_2O$ | 0.0002 |
| agar | 3.0 |

Incubation is preferably carried out at 27° C. The aqueous freezing solution preferably contains about 5% lactose, about 10% glycerol and about 0.05% sodium dodecyl sulfate. The spore mixture is preferably stored at −20° C.

Process step (b) is typically carried out using the entire contents (about 1.0 mL) of a vial of spore mixture to inoculate a 250-mL shake flask containing 30 mL of the medium. The glucose-cottonseed meal-yeast extract medium has the following formula:

| Glucose-Cottonseed Meal-Yeast Extract Medium | |
|---|---|
| Ingredient | % Weight/Volume |
| glucose | 2.0 |
| cottonseed meal (Pharmamedia) | 1.5 |
| yeast extract | 0.5 |
| $(NH_4)_2SO_4$ | 0.3 |
| $ZnSO_4.7H_2O$ | 0.003 |
| $CaCO_3$ (precipitate) | 0.4 |

The medium is autoclaved at 121° C. for 20 minutes after mixing. After incubation the entire contents of the shake flask is transferred to a 2.8 L Fernbach flask containing 500 mL of the glycerol-beef extract medium, which is adjusted to pH 7.0 prior to autoclaving and has the following formula:

| Ingredient | % Weight/Volume |
|---|---|
| glycerol | 3.0 |
| beef extract (BBL #12303) | 3.0 |
| L-tryptophan | 0.1 |
| $K_2HPO_4$ | 0.05 |
| $MgSO_4 \cdot 7H_2O$ | 0.05 |
| KCl | 0.03 |
| $CaCO_3$ | 0.3 |

Both incubations are preferably carried out at 27° C. with agitation at 210 rpm.

In process step (c) the glycerol-beef extract medium has the above-described formula.

In process step (d) the glycerol-ammonia-glutamate medium, which is adjusted to pH 6.5 prior to autoclaving, has the following formula:

| Glycerol-Ammonia-Glutamate Medium | |
|---|---|
| Ingredient | % Weight/Volume |
| glycerol | 6.0 |
| $NH_4Cl$ | 0.15 |
| sodium glutamate | 0.75 |
| KCl | 0.05 |
| $K_2HPO_4$ | 0.01 |
| $MgSO_4 \cdot 7H_2O$ | 0.05 |
| $FeSO_4 \cdot 7H_2O$ | 0.01 |
| $ZnSO_4 \cdot H_2O$ | 0.01 |
| polyethylene glycol (Dow P2000) | 1.0 |

In process step (d) the concentration of 3-(4-morpholino)propanesulfonic acid in the aqueous 3-(4-morpholino)propanesulfonic acid buffer is preferably 50 mM and the buffer has pH 6.7.

In process steps (c) and (d) the incubation is preferably carried out at 27° C. in a 250-mL shake flask at 210 rpm using 30 mL of medium or buffer and 3 mL of cell culture or in a bench top fermentor at 400 rpm sparged with air at 2.5 L/min using 5 L of medium or buffer and 500 mL of cell culture. In a fermentor operated under pH control 6M sulfuric acid is added as needed.

Packed cell volume is used to estimate cell mass by centrifuging 15 mL of whole broth for 10 minutes at 3,500 rpm and estimating the ratio of cell volume to total volume. Packed cell volume increases from less than 5% at inoculation to 35–40% after 48 hours, after which the culture morphology changes from a very fine, highly branched, off-white mycelium to a denser, dark-colored mycelium accompanied by formation of a reddish, soluble pigment, indicating transition from primary to secondary metabolism.

Production of the compound of Formula I wherein $R_1$ and $R_1'$ are both hydrogen and $R_2$ and $R_2'$ are both phenylmethyl by process step (c) or process step (d) using the glycerol-ammonia-glutamate medium is monitored by reverse phase high pressure liquid chromatographic (HPLC) analysis using octadecylated silica gel as adsorbant, methanol-water (65:35) as eluant and detection at 242 nM in the ultraviolet spectrum. At incubating times less than 48 hours after inoculation a mixture of a sample (5 mL) of whole broth is mixed with ethyl acetate (10 mL), the mixture is centrifuged, the ethyl acetate layer is separated and stripped of ethyl acetate, the residue is dissolved in isopropyl alcohol (0.5 mL), and an aliquot thereof (0.01 mL) is analyzed. At times more than 48 hours after inoculation a sample (5 mL) of whole broth is mixed with isopropyl alcohol (5 mL), the mixture is centrifuged, and an aliquot of the supernatant liquid (0.01 mL) is analyzed.

Production of the compound of Formula I wherein $R_1$ and $R_1'$ are both hydrogen and $R_2$ and $R_2'$ are both phenylmethyl (Compound I-1) by process step (c) in a fermentor at 27° C. using the glycerol-beef extract medium gave the following results:

| Production Rate of Compound I-1 Using Glycerol-Beef Extract Medium | |
|---|---|
| Time after Inoculation (hr) | Product/Volume of Whole Broth (μg/mL) |
| 24 | 10 |
| 48 | 20 |
| 72 | 70 |
| 96 | 120 |
| 120 | 130 |
| 144 | 150 |
| 168 | 230 |
| 240 | 270 |

Production of the compound of Formula I wherein $R_1$ and $R_1'$ are both hydrogen and $R_2$ and $R_2'$ are both phenylmethyl (Compound I-1) by process step (c) in a fermentor at 27° C. using the glycerol-beef extract medium and control of the pH below 7.5 gave the following results:

| Production Rate of Compound I-1 Using Glycerol-Beef Extract Medium and pH Below 7.5 | |
|---|---|
| Time after Inoculation (hr) | Product/Volume of Whole Broth (μg/mL) |
| 24 | 10 |
| 48 | 20 |
| 72 | 70 |
| 96 | 120 |
| 120 | 130 |
| 144 | 150 |
| 168 | 230 |
| 240 | 270 |

The compounds of Formula II, which are tryptophan and derivatives thereof, and Formula III, which are a variety of amino acids including especially phenylalanine and derivatives thereof, for use in process step (d) are known and are commercially available or can be prepared by known methods.

Production of the compound of Formula I wherein $R_1$ and $R_1'$ are both hydrogen and $R_2$ and $R_2'$ are both phenylmethyl (Compound I-1) by process step (d) in shake flasks at 27° C. for 7 days using the glycerol-ammonia-glutamate medium and added tryptophan and/or phenylalanine gave the following results:

| Production of Compound I-1 Using Added Tryptophan and/or Phenylalanine | | |
|---|---|---|
| Tryptophan (g/L) | Phenylalanine (g/L) | Product/Volume of Whole Broth (μg/mL) |
| 0 | 0 | 210 |
| 0 | 2 | 475 |
| 2 | 0 | 377 |
| 2 | 2 | 632 |

In process step (d) by direct addition to the cell culture or by addition after washing and resuspending the cell culture in the aqueous 3-(4-morpholino)propanesulfonic acid buffer the compounds of Formula II and Formula III are added as dry powders and the incubation is carried out for 72 hours. The entire incubation mixture is extracted with an equal volume of ethyl acetate and the extract is evaporated to dryness. The residue is dissolved in a minimum volume of dimethylsulfoxide or dimethylformamide, and the solution is subjected to analytical or preparative reverse phase high pressure liquid chromatography (HPLC) using octadecylsilylated silica gel as adsorbant, methanol-water (various fixed and gradient mixtures) as eluant and detection at 241 and 310 nm in the ultraviolet spectrum.

Compound I-1 was prepared by either step (c) or step (d) of the process aspect of the invention. Compounds I-2 through I-40 were prepared by step (d) of the process aspect of the invention. Table I identifies compounds I-1 through I-40 by the amino acid added and each of the four structural variables.

TABLE 1

Compounds of Formula I

| Cpd. | Amino Acid Added | $R_1$ | $R_1'$ | $R_2$ | $R_2'$ |
|---|---|---|---|---|---|
| I-1 | none | H | H | benzyl | benzyl |
| I-2 | 4-fluorotryptophan | 5-F | H | benzyl | benzyl |
| I-3 | 4-fluorotryptophan | 5-F | 5'-F | benzyl | benzyl |
| I-4 | 5-fluorotryptophan | 6-F | H | benzyl | benzyl |
| I-5 | 5-fluorotryptophan | 6-F | 6'-F | benzyl | benzyl |
| I-6 | 6-fluorotryptophan | 7-F | H | benzyl | benzyl |
| I-7 | 6-fluorotryptophan | 7-F | 7'-F | benzyl | benzyl |
| I-8 | o-fluorophenyl-alanine | H | H | o-fluoro-benzyl | benzyl |
| I-9 | o-fluorophenyl-alanine | H | H | o-fluoro-benzyl | o-fluoro-benzyl |
| I-10 | m-fluorophenyl-alanine | H | H | m-fluoro-benzyl | benzyl |
| I-11 | m-fluorophenyl-alanine | H | H | m-fluoro-benzyl | m-fluoro-benzyl |
| I-12 | p-fluorophenyl-alanine | H | H | p-fluoro-benzyl | benzyl |
| I-13 | p-fluorophenyl-alanine | H | H | p-fluoro-benzyl | p-fluoro-benzyl |
| I-14 | 5-methoxy-tryptophan | 6-$CH_3O$ | H | benzyl | benzyl |
| I-15 | 4-methyltryptophan | 5-$CH_3$ | H | benzyl | benzyl |
| I-16 | 4-methyltryptophan | 5-$CH_3$ | 5'-$CH_3$ | benzyl | benzyl |
| I-17 | 5-methyltryptophan | 6-$CH_3$ | H | benzyl | benzyl |
| I-18 | 5-methyltryptophan | 6-$CH_3$ | 6'-$CH_3$ | benzyl | benzyl |
| I-19 | 6-methyltryptophan | 7-$CH_3$ | H | benzyl | benzyl |
| I-20 | 5-bromotryptophan | 6-Br | H | benzyl | benzyl |
| I-21 | o-chlorophenyl-alanine | H | H | o-chloro-benzyl | benzyl |
| I-22 | o-chlorophenyl-alanine | H | H | o-chloro-benzyl | o-chloro-benzyl |
| I-23 | p-chlorophenyl-alanine | H | H | p-chloro-benzyl | benzyl |
| I-24 | p-chlorophenyl-alanine | H | H | p-chloro-benzyl | p-chloro-benzyl |
| I-25 | o-methylphenyl-alanine | H | H | o-methyl-benzyl | benzyl |
| I-26 | o-methylphenyl-alanine | H | H | o-methyl-benzyl | o-methyl-benzyl |
| I-27 | p-methylphenyl-alanine | H | H | p-methyl-benzyl | benzyl |
| I-28 | p-methylphenyl-alanine | H | H | p-methyl-benzyl | p-methyl-benzyl |
| I-29 | methionine | H | H | methyl-thio-methyl | benzyl |
| I-30 | leucine | H | H | 2-methyl-propyl | benzyl |
| I-31 | 5,5,5-trifluoro-leucine | H | H | 2-tri-fluoro-methyl-propyl | benzyl |
| I-32 | valine | H | H | 2-methyl-ethyl | benzyl |
| I-33 | norvaline | H | H | propyl | benzyl |
| I-34 | allylglycine | H | H | 2-pro-penyl | benzyl |
| I-35 | crotylglycine | H | H | 2-butenyl | benzyl |
| I-36 | allylglycine | H | H | 2-butenyl | 2-butenyl |
| I-37 | 3-(2-thienyl)alanine | H | H | 2-thienyl-methyl | benzyl |
| I-38 | 3-(2-thienyl)alanine | H | H | 2-thienyl-methyl | 2-thienyl-methyl |
| I-39 | 3-cyclohexylalanine | H | H | cyclo-hexyl-methyl | benzyl |
| I-40 | 3-cyclohexylalanine | H | H | cyclo-hexyl-methyl | cyclo-hexyl-methyl |

Identification and structural determination including determination of configurations of chiral carbon atoms of the compounds of Formula I is accomplished by known chemical and physical methods including degradation, derivatization, elemental analysis, amino acid analysis, melting range, infrared spectral analysis, ultraviolet spectral analysis, mass spectral analysis, nuclear magnetic resonance spectral analysis, optical rotation and/or circular dichroism spectral analysis.

Compound I-1 and a minor amount of Compound I-30 were obtained by carrying out step (c) of the process aspect of the invention. An incubation mixture of Aspergillus ATCC 74177 in the above-described glycerol-beef extract medium (100 mL) was extracted twice with ethyl acetate (100 mL each time). Separation of the components of the residue (75 mg) from the extracts by flash reverse phase chromatography on octadecylsilylated silica gel and then high pressure liquid chromatography on octadecylsilylated silica gel with methanol-water (3:1) as eluant afforded Compound I-1 (23 mg) and Compound I-30 (1 mg), both as white solids.

Chemical and Physical Properties of the Compounds

Compound I-1 showed the following chemical and physical properties whereby the compound is identified and the structure including the configurations of the chiral carbon atoms thereof was deduced:

Amino acid analysis and Marfey's derivatization showed two (1.8 observed) molecules of L-phenylalanine per molecule of Compound I-1.

Melting range: 203°–205° C.

Infrared spectral analysis ($\tilde{\nu}_{max}$ in $cm^{-1}$): 1670, 1455, 1405, 1335, 1315, 1255, 1215, 1190, 1170, 1100, 745, 700.

Ultraviolet spectral analysis ($\lambda_{max}$ in nM ($\epsilon$) in methanol): 211 (37800), 241 (12100), 301 (5300) indicative of an indoline moiety.

Mass spectral analysis showed at high resolution a peak indicative of the protonated molecular ion $(C_{40}H_{37}N_6O_4)^+$ and at low resolution an intense peak indicative of cleavage of the molecular ion into two equal ions $(C_{20}H_{18}N_3O_2)^+$ and thus indicative of the dimeric structure. Other fragment ions consistent with the proposed structures were also detected.

Proton and carbon-13 magnetic resonance spectral analysis including homonuclear and heteronuclear coupling determinations showed for each half of the molecule five aromatic phenyl (of phenylalanyl) protons, four aromatic (benzenoid ring) indoline protons, two sets of methylene protons ($\beta$-tryptophyl and $\beta$-phenylalanyl), three methine protons (indoline, $\alpha$-tryptophyl and $\alpha$-phenylalanyl) and two exchangeable protons (indoline N-H and diketopiperazine N-H) and two methylene carbon atoms, twelve methine carbon atoms and six quaternary carbon atoms with chemical shifts and coupling constants consistent with Formula I wherein $R_1$ and $R_1'$ are both hydrogen and $R_2$ and $R_2'$ are both benzyl. The coupling constant between the α-tryptophyl and α-phenylalanyl (11- and 15-positions of Formula I) protons indicated that they are cis.

Optical rotation: $[α]_D+200.0$ (0.15% by weight/volume in methanol).

Degradation of Compound I-1 (10 mg) with trifluoroacetic acid (1 mL) with stirring at room temperature for ten minutes, removal of trifluoroacetic acid under vacuum and purification of the residue by high pressure liquid chromatography gave the known diketopiperazine derivative of L-tryptophyl-L-phenylalanine, which was identified by infrared spectral analysis, ultraviolet spectral analysis, mass spectral analysis, proton and carbon-13 magnetic resonance spectral analysis, circular dichroism spectral analysis and synthesis, thus establishing the configurations of the four diketopiperazine (α-tryptophyl and α-phenylalanyl) methine carbon atoms as S.

Methylation of Compound I-1 (500 mg) with methyl iodide (1.5 mL) and potassium carbonate (500 mg) in acetone (2.0 mL) with stirring at room temperature for twenty hours followed by filtration and removal of methyl iodide and acetone from the filtrate under vacuum and separation of the components of the residual mixture by high pressure liquid chromatography gave the derivative of Compound I-1 wherein one of the secondary diketopiperazine nitrogen atoms is methylated (Monomethyl Compound I-1; 15 mg; m.r. 196°–198° C.; $[α]_D+170.3$, 0.35% by weight/volume in methanol) and the derivative of Compound I-1 wherein both of the secondary diketopiperazine nitrogen atoms are methylated (Dimethyl Compound I-1; 12 mg; m.r. 198°–201° C.; $[α]_D+140.0$, 0.30% by weight/volume in methanol).

Oxidative cyclization of the known diketopiperazine derivative of L-tryptophyl-L-phenylalanine (100 mg) by the known method of irradiating a methanol (100 mL) solution thereof in the presence of rose bengal (10 mg) at ice bath temperature overnight followed by separation of the products by flash chromatography on silica gel and then high pressure liquid chromatography gave known Compound IVa (8 mg) of Formula IVa and known Compound IVb (9 mg) of Formula IVb, which were identified by infrared spectral analysis, ultraviolet spectral analysis, mass spectral analysis, proton and carbon-13 magnetic resonance spectral analysis and optical rotation.

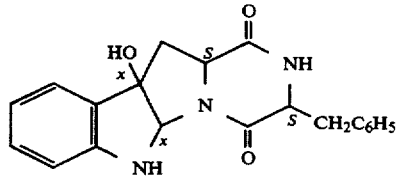

Formula IVa: X = R
Formula IVb: X = S

Comparative circular dichroism spectral analysis of Compound I-1, ditryptophenaline prepared as described below, Compound IVa and Compound IVb showed curves having positive displacements at approximately 240 nM and 300 nM for Compound I-1 and Compound IVa and curves having negative displacements at approximately the same wavelengths for ditryptophenaline and Compound IVb, thus indicating that the configuration of each of the four quaternary indoline carbon atoms of Compound I-1 is R.

Difference nuclear Overhauser enhancement spectroscopy gave direct evidence that the configuration of each of the four quaternary indoline carbon atoms of Compound I-1 is R. Enhancements were observed between the following three pairs of protons within each monomeric unit, each proton of which is identified parenthetically by its position in Formula I: 2-indoline(2,2')-α-tryptophyl (11,11'), 4-indoline(5,5')-axial-(β-tryptophyl)(12b,12b'), α-tryptophyl (11,11')-equatorial-(β-tryptophyl)(12a,12a'). That the enhancements occurred within each monomeric unit and not between monomeric units was shown by comparison of the results of Monomethyl Compound I.

The corresponding carbon atoms of ditryptophenaline have the S-configuration as shown by x-ray crystallographic analysis (Springer et al. reference cited above), which established relative configurations, and synthesis (Nakagawa et al., Tetrahedron Letters, 22(52), pp. 5323–5326, 1981), which established absolute configurations. Each of the four diketopiperazine (α-tryptophyl and α-phenylalanyl) methine carbon atoms has the S-configuration in both compounds. Both of the secondary diketopiperazine nitrogen atoms of ditryptophenaline are methylated. Dimethyl Compound I-1 wherein both of the secondary diketopiperazine nitrogen atoms of Compound I-1 are methylated is not identical with ditryptophenaline. Dimethyl Compound I-1 and ditryptophenaline have optical rotations of opposite sign. Since only two such compounds having the favorable cis junction between the pyrrolidine rings are possible and ditryptophenaline is one of them, Dimethyl Compound I-1 is the other one and differs from ditryptophenaline by having the R-configuration instead of the S-configuration at each of the four quaternary indoline carbon atoms thereof.

Energy dependent conformations of Compound I-1 and Monomethyl Compound I-1 in solution were determined by computer assisted analysis and proton and carbon-13 magnetic resonance spectral data.

Compound I-30 showed the following chemical and physical properties whereby the compound is identified and the structure including the configurations of the chiral carbon atoms thereof was deduced as being analogous to that of Compound I-1:

Amino acid analysis and Marfey's derivatization showed one (0.8 observed) molecule of L-leucine and one (1.3 observed) molecule of L-phenylalanine per molecule of Compound I-30.

Melting range: 194°–196° C.

Infrared spectral analysis ($v_{max}$ in cm$^{-1}$): 1670, 1480, 1410, 1310, 1315, 1255, 1200, 1100, 750, 700.

Ultraviolet spectral analysis ($λ_{max}$ in nM (ε) in methanol): 213 (35500), 242 (10000), 301 (4500) indicative of an indoline moiety.

Mass spectral analysis showed at high resolution a peak indicative of the protonated molecular ion $(C_{37}H_{39}N_6O_4)^+$ and at low resolution peaks indicative of cleavage of the molecular ion into the ion $(C_{20}H_{18}N_3O_2)^+$ corresponding identically to one of the monomers of Compound I-1, and the ion $(C_{17}H_{20}N_3O_2)^+$ corresponding to the other monomer of Compound I-1 but having the leucine side chain $(C_4H_9)$ instead of the phenylalanine side chain $(C_7H_7)$.

Proton and carbon-13 magnetic resonance spectral analysis including homonuclear coupling determinations showed chemical shifts and coupling constants consistent with Compound I-1 and with the leucylphenylalanyl difference.

Optical rotation: $[\alpha]_D + 280.0$ (0.012% by weight/volume in methanol).

The circular dichroism spectrum of Compound I-30 is similar to that of Compound I-1.

Characterization and structural determination of the remaining compounds of Table I was accomplished by spectral analysis and comparison of the results with those of Compounds I-1 and I-30. Analytical high pressure liquid chromatographic analysis and ultraviolet spectral analysis were used for preliminary identification. The molecular ion and the two monomeric fragment ions of each compound were determined by low resolution mass spectral analysis and the results were confirmed by high resolution mass spectral analysis of Compounds I-(4–11), (15–18), (20–22), 25, 27, 28, 29, 35 and 36. Proton and carbon-13 magnetic resonance spectral analysis including homonuclear coupling determinations and circular dichroism spectral analysis were performed on Compounds I-(4–11), 35 and 36.

BIOLOGICAL PROPERTIES OF THE COMPOUNDS

As stated above the compounds of Formula I are useful as Substance P antagonists and therefore as analgesic and/or antiinflammatory agents. Substance P antagonist NK1 receptor binding activity was determined using guinea pig submaxillary gland tissue and human astrocytoma cells.

Submaxillary glands from both sexes of Hartley guinea pigs were obtained from Pel Freeze Biologicals, Rogers, Arkansas by overnight express in a plastic bag kept cold in wet ice. Extraneous tissue was removed and the glands were homogenized (Brinkman Polytron 10TS generator, 3–4 10-second bursts at a setting of 10) in ice cold buffer C (sodium chloride, 120 mM; potassium chloride, 5 mM; tromethamine [TRIS], 50 mM; pH adjusted to 7.40 with dilute hydrochloric acid; 100 mL for 50 submaxillary glands). The homogenate was centrifuged (16,000×g) at 4° C. for 15 minutes and the supernatant fluid was discarded. In order to release any native bound Substance P from its receptor approximately 200 mL of buffer B (potassium chloride, 500 mM; tromethamine, 50 mM; ethylenediaminetetraacetic acid [EDTA], 10 mM; pH adjusted to 7.40 with dilute hydrochloric acid) was added to the pellet, which was resuspended by low speed homogenization. The suspension was incubated at ice temperature for 30 minutes with periodic swirling and centrifuged, and the supernatant liquid was discarded. Tromethamine buffer (50 mM, pH adjusted to 7.40 with dilute hydrochloric acid, 200 mL) was added, the pellet was resuspended, the suspended mixture was centrifuged, the supernatant fluid was discarded, and this procedure was repeated. About twice the pellet volume of tromethamine buffer was added to the pellet and the resulting submaxillary gland tissue preparation (1.0 to 1.5 mL) was stored at $-70°$ C. Using serum bovine albumin as the standard the protein yield was determined by the Bradford method (Bio-Rad, Richmond, Calif.) to be 7–8 mg/mL or about 250 mg from 50 submaxillary glands.

To test for receptor binding a sample of the submaxillary gland tissue preparation was thawed on ice and rehomogenized with a glass homogenizer (Dounce). To a polystyrene test tube were added an aliquot of the resulting homogenate (200 μL containing 150–300 μg of protein), tromethamine buffer (100 μL), protease buffer (aqueous chymostatin, 5 μg/mL; leupeptin, 10 μg/mL; bacitracin, 100 μg/mL; manganous chloride, 3 mM; bovine serum albumin, 0.05%; tromethamine, 50 mM; pH adjusted to 7.40 with dilute hydrochloric acid; 100 μL) and tritiated Substance P (44–54 Ci/millimole, 0.75 nM in protease buffer, 100 μL). Dimethylsulfoxide alone (5 μL) or a dimethylsulfoxide solution (5 μL) of the test compound (amount such that 1:100 dilution gave the desired concentration thereof) was added to the tube. The mixture was allowed to reach equilibrium for 20–30 minutes, then filtered (Whatman GF/C filter, Brandel harvester). The residue on the filter was washed three times with tromethamine buffer (3 mL each time) and its radioactivity was measured in a liquid scintillation counter (Beckman LS5000) (x=number of counts per minute with test compound, y=number of counts per minute without test compound). Adding a large excess of untritiated Substance P (1 μM) to the protease buffer and carrying out the procedure without test compound gave a measure (z=number of counts per minute) of the nonspecific binding, which was generally less than 10% of the total binding. The dissociation constant ($K_d$) for receptor binding was determined by varying the concentration of tritiated Substance P. The following calculations were made:

% bound = 100(x−z)/(y−z)

% inhibition = % bound − 100

L = ln(% inhibition/% bound).

Values of L for each test compound were plotted against the corresponding values of the log of the concentration of the test compound, a linear regression line was constructed, and the concentration of the test compound corresponding to L=0, which is defined as the IC$_{50}$ value, was determined. The inhibitor affinity constant ($K_i$) for each test compound was then calculated according to Cheng and Prusoff (Biochem. Pharmacol., vol. 22, p. 3099, 1973) as follows:

$$K_i = IC_{50}/(1 + 0.75/K_d)$$

Human astrocytoma cells (U—373 MG, ATCC No. HTB 17) were cultured in 75-mL flasks in an aqueous medium containing horse serum (heat inactivated, 10%), minimum essential amino acids (2%), minimum essential vitamin solution (2%), and an aqueous solution of penicillin (10,000 units/mL) and streptomycin (10,000 μg/mL) (Penn-Strep, 2%), which was sterilized by filtration through a disposable filter (Nalgene, VWR Cat. No. 28199–585). The medium was replaced twice weekly. Cells were passaged (1:4 split) by removing the medium and adding aqueous trypsin (0.25%, 8 mL/flask). The flasks were swirled for 30 seconds, the aqueous trypsin was removed, and the cells were incubated for 5 minutes at room temperature, then washed twice with fresh medium (7 mL each time). Poly-D-lysine solution (50 μg/mL in aqueous phosphate saline buffer, 0.25 mL) was added to each well of a sterile 96-well ceramic plate (Corning), which was then incubated at room temperature for 40 minutes. The poly-D-lysine solution was removed, each well was washed twice with aqueous phosphate saline buffer (0.25 mL), cells were added (0.2 mL/well), and the plate was incubated at 37° C. for two days in an oxygen-carbon dioxide (95:5) atmosphere to provide a monolayer of 1.4–1.9×10$^4$ cells per well.

To test for receptor binding the aqueous phosphate saline buffer was removed from each well, the cell monolayer was washed three times with assay buffer (aqueous 2-[4-(2-hydroxyethyl)-1-piperazinyl]ethanesulfonic acid [HEPES], 25 mM; potassium chloride, 5.8 mM; monopotassium phosphate, 2.2 mM; sodium chloride, 115 mM; magnesium sulfate, 0.6 mM; calcium chloride, 1.8 mM; bovine serum albumin, 1%; glucose, 5 mM; thiorphan, 1 μM; and bacitracin, 40 μg/mL; pH adjusted to 7.40 with dilute hydrochloric acid; 0.25 mL each time). To each well was then added assay buffer alone (0.1 mL) or a mixture (0.1 mL) with assay buffer as diluent containing $^{125}$I-Bolton Hunter Substance P (Amersham, Inc., Arlington Heights, Ill.; 0.1 nanomole) and test compound in amount to give the desired concentration thereof or, to determine nonspecific binding, unlabelled Substance P (0.1 micromole) and the plate was incubated at 25° C. for 90 minutes. Excess assay buffer or Substance P mixture was then removed and each well was washed four times with assay buffer (0.25 mL each time). The cells were detached from each well by addition of aqueous octoxynol (Triton X-100, 0.2%, 140 μL) containing bovine serum albumin (1 mg/L). The radioactivity of part (100 μL) of the detachment mixture was measured in a gamma ray counter (Packard Cobra). $K_d$ and $IC_{50}$ values were determined and a $K_i$ value was calculated for each test compound as described above.

Table II presents Substance P antagonist $K_i$ values of the compounds of Formula I of Table I tested in guinea pig submaxillary gland tissue and/or human astrocytoma cells except Compound I-12, which was not sufficiently pure for testing.

TABLE II

Substance P Antagonist Potencies of Compounds of Formula I

| Compound | $K_i$ (μM) | |
|---|---|---|
| | Guinea Pig Submaxillary Gland Tissue | Human Astrocytoma Cells |
| I-1 | 0.95–2.40 | 0.24 |
| I-2 | 6.37 | |
| I-3 | >40.00 | |
| I-4 | 9.50 | 1.85 |
| I-5 | 20.00 | 2.85 |
| I-6 | 2.27 | 0.26 |
| I-7 | 1.57 | 0.17 |
| I-8 | | 0.70 |
| I-9 | 5.80 | 0.63 |
| I-10 | 2.56 | 0.38 |
| I-11 | 1.14 | 0.17 |
| I-13 | 4.60 | |
| I-14 | 0.90 | |
| I-15 | | 0.44 |
| I-16 | | 5.65 |
| I-17 | | 0.59 |
| I-18 | | 2.85 |
| I-19 | 7.80 | |
| I-20 | | 1.50 |
| I-21 | | 0.26 |
| I-22 | | 0.22 |
| I-23 | 2.86 | |
| I-24 | >40.00 | |
| I-25 | | 0.19 |
| I-26 | | 0.16 |
| I-27 | | 0.35 |
| I-28 | | 0.45 |
| I-29 | 3.70 | |
| I-30 | 4.10 | 3.95 |
| I-31 | 7.58 | |
| I-32 | 22.80 | |
| I-33 | >40.00 | |
| I-34 | 5.80 | |
| I-35 | 3.20 | 2.05 |
| I-36 | >40.00 | 11.00 |
| I-37 | | 0.93 |
| I-38 | | 3.00 |
| I-39 | | 0.38 |

TABLE II-continued

Substance P Antagonist Potencies of Compounds of Formula I

| Compound | $K_i$ (μM) | |
|---|---|---|
| | Guinea Pig Submaxillary Gland Tissue | Human Astrocytoma Cells |
| I-40 | | 0.80 |

In other tests Compound I-1 was found to inhibit $^{125}$I-neurokinin A binding to the NK2 receptor in both rat duodenum and human urinary bladder membranes at comparable $K_i$ values of 0.26 μM and 0.72 μM respectively. The inhibitory effect of Compound I-1 against the NK3 selective ligand $^3$H-senktide tested in a guinea pig forebrain membrane preparation was found to be much weaker ($IC_{50}$=15.2 μM). Compound I-1 was also evaluated in NK1 functional assays and was found to be a competitive inhibitor of Substance P-induced contractility in the guinea pig ileum (pA$_2$=6.6±0.31) as well as an inhibitor of Substance P-induced $^{45}$Ca$^{2+}$ efflux from human astrocytoma U373MG cells ($IC_{50}$=0.6±0.3 μM). In a rat vas deferens model Compound I-1 inhibited eledoisin-induced contractility with an $IC_{50}$ value of 3.4±1.3 μM indicative of functional antagonism at the NK2 receptor.

COMPARATIVE TEST OF DITRYPTOPHENALINE

*Aspergillus flavus* SC1661 (formerly MIT-M26, obtained from Arnold Demain at Massachusetts Institute of Technology) was grown on supplemented cracked corn (500 mL) and the fermentation mixture was extracted twice with ethyl acetate (200 mL each time). The ethyl acetate extract was stripped of ethyl acetate. Fatty material was removed from the residue by trituration with hexane and the remaining material was subjected to reverse phase high pressure liquid chromatography on octadecylsilated silica gel (Waters, RCM). Ditryptophenaline was obtained as a white solid (8 mg). Results of ultraviolet spectral analysis, mass spectral analysis, nuclear magnetic resonance spectral analysis and optical rotation determination were in agreement with literature results. Circular dichroism spectral analysis results were in agreement with those of Nakagawa et al. (Tetrahedron Letters, 22(52), pp. 5323–5226, 1981) but not those of Maes et al. (Journal of the Chemical Society, Perkin Transactions 1, 1986, pp 861–866), which appear to be in error. In the test for Substance P antagonist activity in human astrocytoma cells ditryptophenaline showed an $IC_{50}$ value of 12.0 μM. In the same test Compound I-1 showed an $IC_{50}$ value of 0.3 μM and was thus shown to be fortyfold more potent than ditryptophenaline.

We claim:

1. A compound having the structural formula

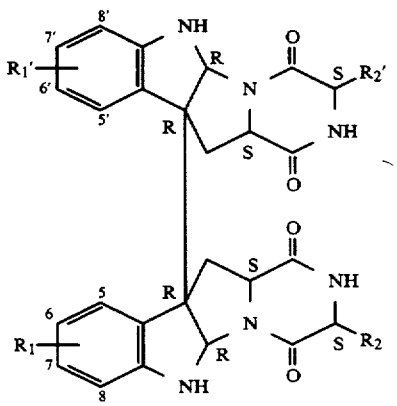

Formula I wherein

R₁ and R₁' are the same or different and are selected from the group consisting of hydrogen, halo, lower-alkyl and lower-alkoxy;

R₂ and R₂' are the same or different and are selected from the group consisting of phenyl-lower-alkyl wherein phenyl is unsubstituted or substituted by halo or lower-alkyl, lower-alkyl except methyl, lower-alkylthio-lower-alkyl, trifluoromethyl-lower-alkyl, lower-alkenyl, thienyl-lower-alkyl and lower-cycloalkyl-lower-alkyl; and R and S represent in each instance the steric configuration of the adjacent carbon atom.

2. A compound according to claim 1 wherein

R₁ and R₁' are the same or different and are selected from the group consisting of hydrogen, fluoro, bromo, methyl and methoxy;

R₂ and R₂' are the same or different and are selected from the group consisting of benzyl benzyl wherein phenyl thereof is substituted by fluoro, chloro or methyl, propyl, 2-methylethyl, 2-methylpropyl, methylthiomethyl, 2-trifluoromethylpropyl, 1-propenyl, 2-propenyl, 2-thienylmethyl and cyclohexylmethyl.

3. A compound according to claim 2 wherein

R₁ and R₁' are the same or different and are selected from the group consisting of hydrogen, 5- or 5'-fluoro, 6- or 6'-fluoro, 7- or 7'-fluoro, 6- or 6'-bromo, 5- or 5'-methyl, 6- or 6'-methyl, 7- or 7'-methyl, and 6- or 6'-methoxy;

R₂ and R₂' are the same or different and are selected from the group consisting of benzyl benzyl wherein phenyl thereof is substituted by o-, m- or p-fluoro, o- or p-chloro or o- or p-methyl, propyl, 2-methylethyl, 2-methylpropyl, methylthiomethyl, 2-trifluoromethylpropyl, 1-propenyl, 2-propenyl, 2-thienylmethyl and cyclohexylmethyl.

4. The compound according to claim 3 wherein R₁ and R₁' are both hydrogen and R₂ and R₂' are both benzyl.

* * * * *